US009000393B2

(12) United States Patent
Takasawa

(10) Patent No.: US 9,000,393 B2
(45) Date of Patent: Apr. 7, 2015

(54) X-RAY IMAGING APPARATUS AND METHOD FOR OUTPUTTING X-RAY IMAGES

(71) Applicant: Canon Kabushiki Kaisha, Tokyo (JP)

(72) Inventor: Toru Takasawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/251,868

(22) Filed: Apr. 14, 2014

(65) Prior Publication Data

US 2014/0219421 A1 Aug. 7, 2014

Related U.S. Application Data

(63) Continuation of application No. 13/216,704, filed on Aug. 24, 2011, now Pat. No. 8,735,845.

(30) Foreign Application Priority Data

Sep. 8, 2010 (JP) .................................. 2010-201342

(51) Int. Cl.
G01T 1/16 (2006.01)
A61B 6/00 (2006.01)
G01J 1/42 (2006.01)

(52) U.S. Cl.
CPC . G01T 1/16 (2013.01); A61B 6/461 (2013.01); G01J 1/42 (2013.01); A61B 6/465 (2013.01)

(58) Field of Classification Search
CPC ....................................................... G01T 1/00
USPC ................................................. 250/394, 395
See application file for complete search history.

(56) References Cited

U.S. PATENT DOCUMENTS

| 4,851,678 | A | 7/1989 | Adachi et al. ................. 250/587 |
| 5,042,060 | A | 8/1991 | Sakakihara ................... 378/173 |
| 5,828,794 | A | 10/1998 | Katayama et al. ............. 382/298 |
| 6,671,394 | B1 | 12/2003 | Sako ............................. 382/132 |
| 6,885,770 | B2 | 4/2005 | Matsuura ....................... 382/199 |
| 7,558,440 | B2 | 7/2009 | Sako et al. .................... 382/298 |
| 2010/0150311 | A1 | 6/2010 | Takasawa ....................... 378/98 |

FOREIGN PATENT DOCUMENTS

| JP | 2000-115513 | 4/2000 |
| JP | 2001-307064 | 11/2001 |
| JP | 2004-000529 | 1/2004 |
| JP | 2006-296954 | 11/2006 |

*Primary Examiner* — David Porta
*Assistant Examiner* — Faye Boosalis
(74) *Attorney, Agent, or Firm* — Fitzpatrick, Cella, Harper & Scinto

(57) ABSTRACT

An X-ray imaging apparatus, which acquires an X-ray photographic image of an subject and outputs the X-ray photographic image to a plurality of output apparatuses, determines, as an output region to a first output apparatus, either an extracted irradiated region from an X-ray photographic image or a partial region selected from the X-ray photographic image by an user. When the size of the output region to the first output apparatus is not larger than an image size to be output to a second output apparatus, the output region to the first output apparatus is determined as an output region to the second output apparatus. When the output region to the first output apparatus is larger than the image size, a region corresponding to the image size is extracted from the output region to the first output apparatus as an output region to the second output apparatus.

30 Claims, 13 Drawing Sheets

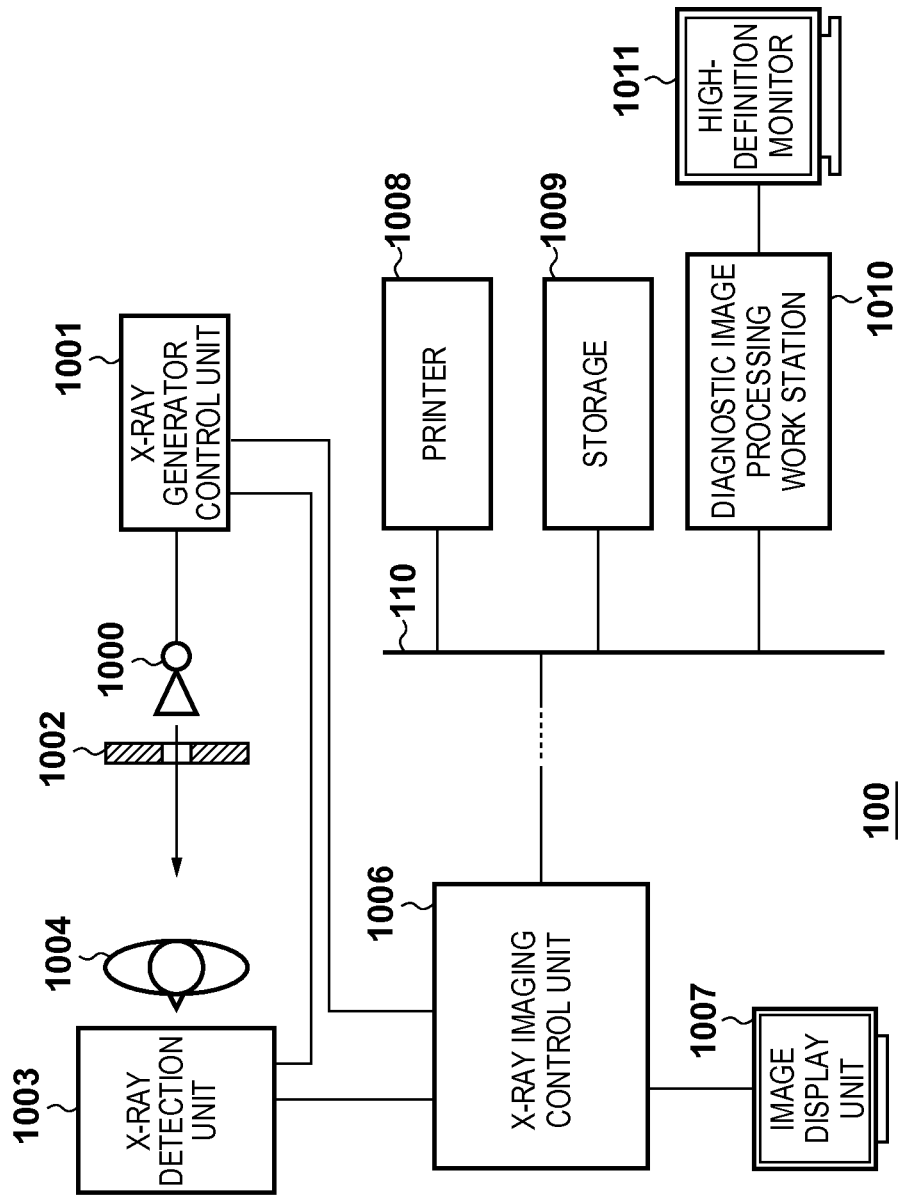

RESOLUTION OF SENSOR

RESOLUTION OF PRINTER

| INCH SIZE | DESIGNATION | ORIENTATION | PIXEL PITCH | PIXEL NUMBER |
|---|---|---|---|---|
| 14×17 | HALF SIZE-PORTRAIT | PORTRAIT | 80μm | 4268×5108 |
| 17×14 | HALF SIZE-LANDSCAPE | LANDSCAPE | 80μm | 5108×4268 |
| 11×14 | LARGE QUARTER-PORTRAIT | PORTRAIT | 80μm | 3388×4277 |
| 14×11 | LARGE QUARTER-LANDSCAPE | LANDSCAPE | 80μm | 4277×3388 |
| 10×12 | QUARTER-PORTRAIT | PORTRAIT | 80μm | 3245×3884 |
| 12×10 | QUARTER-LANDSCAPE | LANDSCAPE | 80μm | 3884×3245 |

F I G. 5
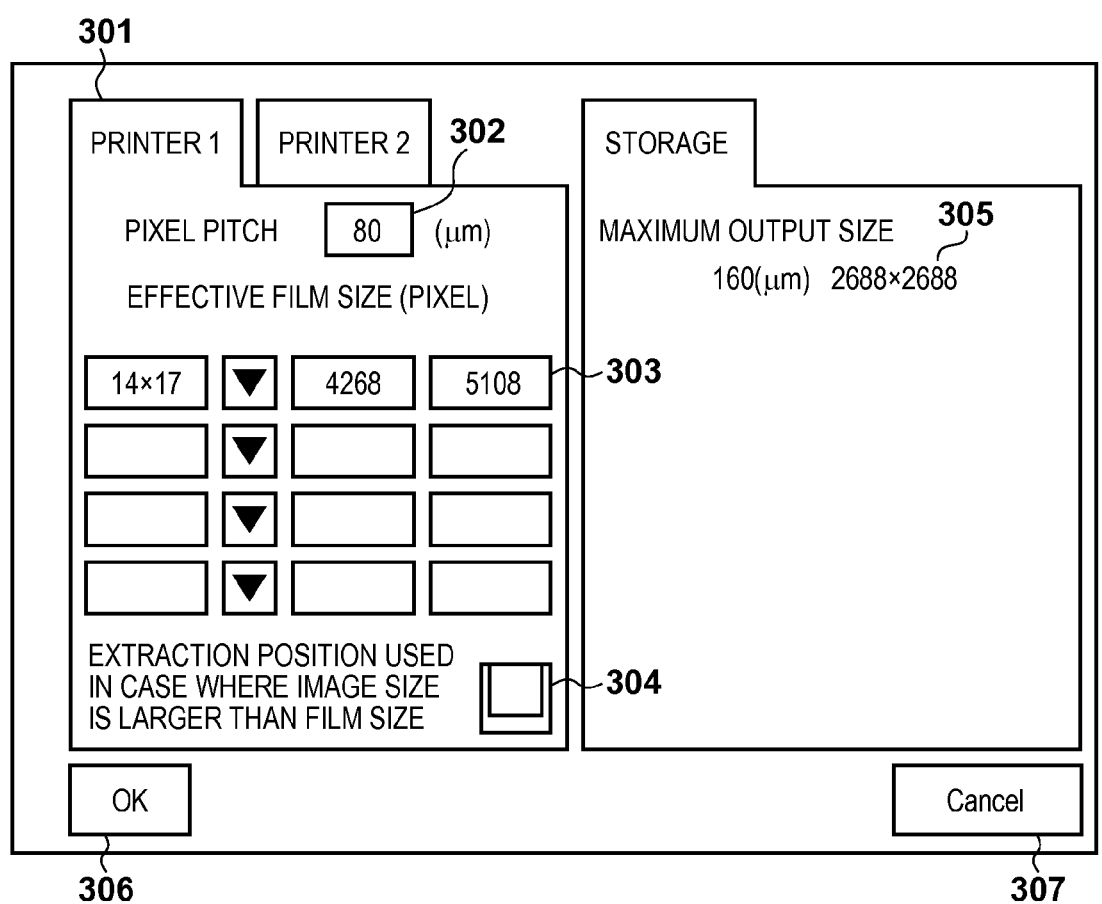

F I G. 10
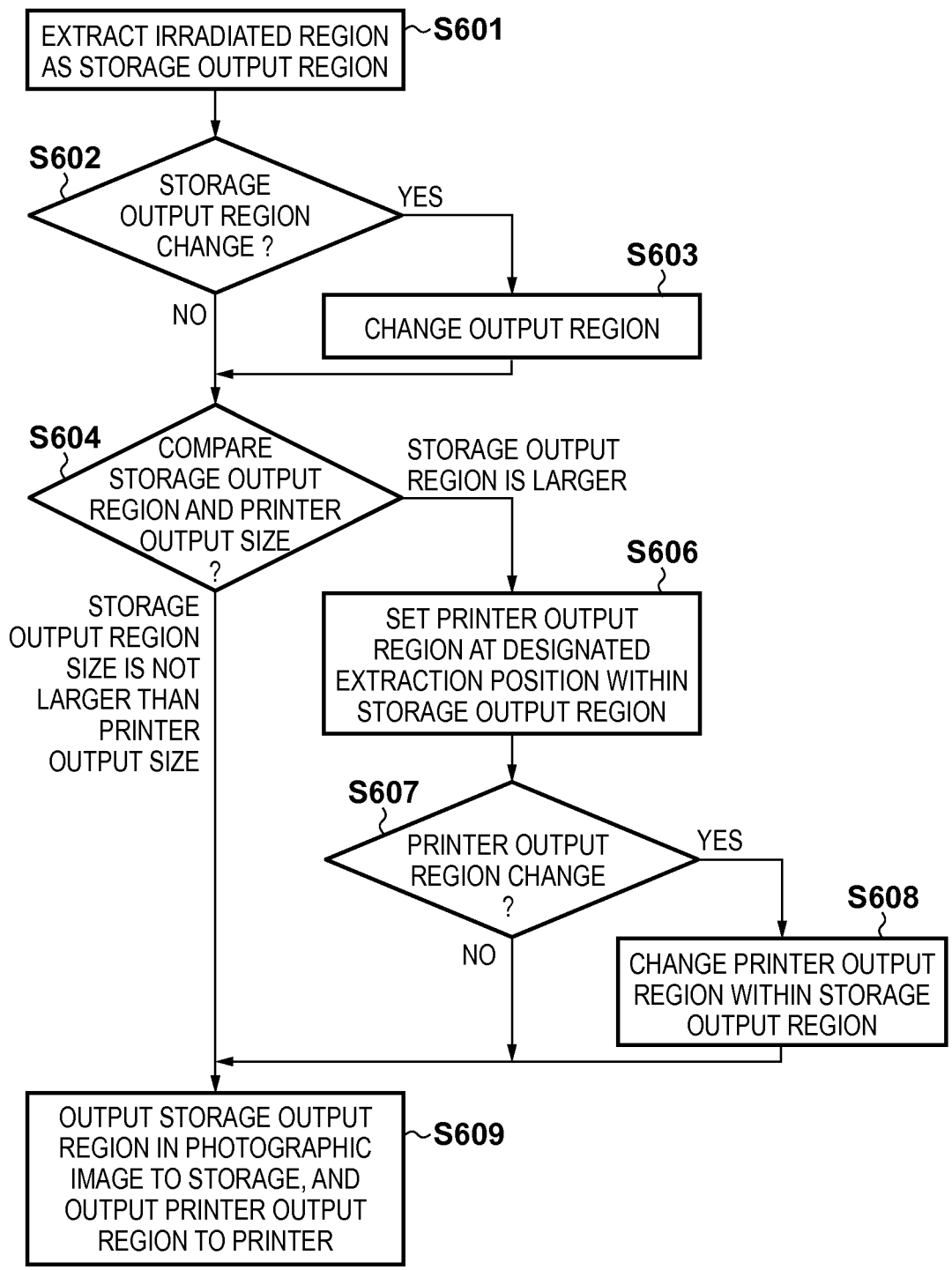

X-RAY IMAGING APPARATUS AND METHOD FOR OUTPUTTING X-RAY IMAGES

This application is a continuation of application Ser. No. 13/216,704, filed Aug. 24, 2011. It claims benefit of that application under 35 U.S.C. §120, and claims benefit under 35 U.S.C. §119 of Japanese Patent Application No. 2010-201342, filed on Sep. 8, 2010. The entire contents of each of the mentioned prior applications are incorporated herein by reference.

BACKGROUND OF THE INVENTION

1. Field of the Invention

The present invention relates to an X-ray imaging apparatus that picks up an image of a subject. In particular, the present invention relates to an X-ray imaging apparatus that suitably adjusts the size of an X-ray photographic image when outputting the image to a plurality of output devices and a method for outputting the X-ray images.

2. Description of the Related Art

As an imaging technique for X-ray imaging apparatus for medical diagnosis, techniques of digitally detecting X-rays and generating X-ray images have been achieving widespread use instead of an X-ray photographic method in which an intensifying screen and a film are used in combination at an X-ray detection unit. As an example of a typical digital X-ray imaging apparatus, there is a digital X-ray imaging apparatus in which a flat-panel sensor is used as a detection device. As X-ray imaging acquisition methods used in digital X-ray imaging apparatus using a flat-panel sensor, there are: a method in which solid-state imaging devices, which are sensitive to X-rays and convert the detected X-rays into electric signals corresponding to the intensity of the X-rays to output the signals, are used, the analog signals from the solid-state devices are converted to digital signals, and the signals are captured for imaging; and a method in which a phosphor, which absorbs the energy of X-rays and emits fluorescence corresponding to the intensity of the energy, and photoelectric conversion elements, which are sensitive to visible light and convert the visible light into electric signals corresponding to the intensity of the visible light, are combined together, the analog signals from the photoelectric conversion elements are converted to digital signals, and the signals are captured for imaging.

Such digital X-ray imaging apparatuses are each constituted by an inspection module and a control unit for controlling the inspection module and an X-ray generator. The inspection module includes a detection device that detects an electrical quantity that corresponds to an X-ray transmission dose and that converts the electrical quantity to a digital quantity. The control unit subjects a captured image to various kinds of correction processing and image processing to generate an X-ray digital image for diagnosis by a doctor. The generated digital image is output from a printer onto a film, or is sent to a storage and displayed on a monitor as necessary, following which the digital image is observed by a doctor.

However, since the size of each film is predetermined, depending on a subject's height and weight, there are cases where an observation region in an image does not completely fit onto a film. In such a case, as described in Japanese Patent Laid-Open No. 2000-115513 (hereinafter referred to as "Document 1"), the orientation of a film is changed, extraction processing is carried out to fit a necessary region in an observation region onto a film, or the entire observation region is reduced so that the region fits onto a film. Of the above methods, the method of reducing the entire observation region to fit the region onto a film is generally not used, because reduction ratios differ depending on the sizes of observation regions, so it is hard to make diagnoses, and this may lead to misdiagnoses. In cases where an X-ray photograph is used for diagnosis, an output mode is used that is either life-size output in which an image on a sensor is output in actual size or fixed reduction ratio output in which an image is output at a fixed reduction ratio.

In a case where an observation region has not completely fitted onto a film even with a film's orientation changed in these output modes, a necessary region has been extracted from the observation region, and has been output to a printer and a storage in a diagnostic image processing work station. In such a method, however, the size of an image to be output to the storage is limited to an output size of the printer, and an image across the entire observation region cannot be obtained when having called up the image on an X-ray interpretation work station. Because of this, in a case where there has been an informative diagnostic point outside the extracted region, there is a possibility that the point was missed. To solve such problems, an operator has to call up an image after the image was output to the printer, change the size of the image, and output the image to the storage again. Therefore, imaging operation becomes complicated, and thus operation efficiency worsens.

Japanese Patent Laid-Open No. 2006-296954 (hereinafter referred to as "Document 2") states that an irradiated region is output to a storage and that an extracted image is output to a printer. In Document 2, however, there is no description of performing a suitable extraction adjustment on an image for image output to the storage and the printer. In cases where an image size is determined by image viewer specifications and where only a fit display mode is enabled, the output size is sometimes limited even in the case of output to a storage. In those cases, there has been a problem in that in a case where it is impossible to subject an image to be output to a storage to extraction adjustment as in Document 2, an error occurs in executing the output to the storage, and it is, therefore, impossible to output the image. It should be noted that "fit display" means that an image is displayed to the maximum extent in a predetermined image display region with the aspect ratio of the displayed image maintained.

SUMMARY OF THE INVENTION

The present invention is carried out in view of such problems; therefore an aspect of the present invention provides an X-ray imaging apparatus in which operability, when outputting an X-ray image to a plurality of output apparatuses having different suitable image sizes, is improved, and provides a method for outputting X-ray images.

According to one aspect of the preset invention there is provided a method for outputting X-ray images, using an X-ray imaging apparatus that acquires an X-ray image of an subject and outputs the X-ray image to a plurality of output apparatuses, the method comprising the steps of: acquiring a first partial image by, when the size represented by the number of pixels of an irradiated region in the X-ray image is larger than the size represented by the number of pixels of a display region of a display unit, extracting a portion of a size not larger than the size of the display region from the irradiated region in the X-ray image; acquiring a second partial image by, when the size given in life size of the first partial image is larger than the size given in life size of an image that can be output by a printer, extracting a portion of a size not larger than the size of the outputtable image is extracted from the first partial image; outputting the first partial image to a storage apparatus; and outputting the second partial image to the printer.

Also, according to another aspect of the present invention, there is provided an X-ray imaging apparatus that acquires an X-ray image of a subject and outputs the X-ray image to a plurality of output apparatuses, the X-ray imaging apparatus comprising: a first acquisition unit that acquires a first partial image by, when a size represented by the number of pixels of an irradiated region in the X-ray image is larger than a size represented by the number of pixels of a display region of a display unit, extracting a portion of a size not larger than the size of the display region from the irradiated region in the X-ray image; and a second acquisition unit that acquires a second partial image by, when the size given in life size of the first partial image is larger than the size given in life size of an image that can be output by a printer, extracting a portion of a size not larger than the size of the outputtable image from the first partial image.

Further features of the present invention will become apparent from the following description of exemplary embodiments with reference to the attached drawings.

BRIEF DESCRIPTION OF THE DRAWINGS

FIG. 1 is a block diagram of a configuration example of an X-ray digital imaging system.

FIG. 5 is an illustration of an example of an output size setting screen according to a first embodiment.

FIG. 10 is a flowchart of image output region determination processing according to the first embodiment.

DESCRIPTION OF THE EMBODIMENTS

Figure 2A:
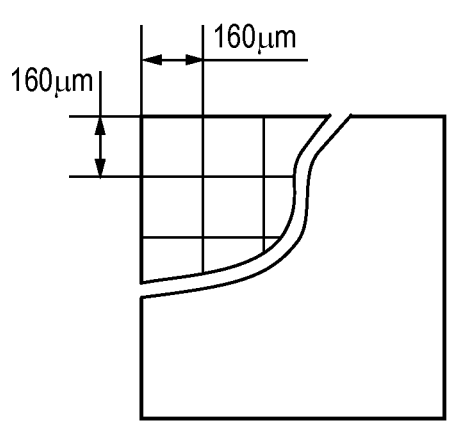
FIGS. 2A and 2B are explanatory drawings of a life-size output.

Some embodiments of the present invention will be described in detail below with reference to the accompanying drawings.

First Embodiment

FIG. 1 is a block diagram of a configuration example of an X-ray imaging system 100 according to a first embodiment to which the present invention is applied. In this embodiment, the X-ray imaging system 100 has a configuration in which the X-ray imaging apparatus (that includes an X-ray generator control unit 1001, an X-ray detection unit 1003, an X-ray imaging control unit 1006, and an image display unit 1007) is connected to a network 110. Through the utilization of such a configuration, the X-ray imaging apparatus outputs an X-ray photographic image to a plurality of output devices connected to the network 110. As the plurality of output devices, a storage 1009 (as a first output device) and a printer 1008 (as a second output device) are connected to the network 110 in this embodiment.

The X-ray imaging system 100 includes an X-ray tube 1000 that generates X-rays, an X-ray exposure field aperture 1002 that is placed in front of the X-ray tube 1000 and prevents unwanted X-ray radiation, and the X-ray generator control unit 1001 that controls the X-ray tube 1000. It should be noted that the X-ray generator control unit 1001 is provided with an operator console (not shown). And further, in the X-ray imaging system 100, the X-ray detection unit 1003 is provided with a flat-panel sensor to detect an X-ray that has been radiated from the X-ray tube 1000 and has passed through a subject 1004. The X-ray imaging control unit 1006 controls the X-ray detection unit 1003 in order to obtain a digital image signal, subjects the digital image signal to predetermined image processing, and performs image output for image display, image printing or the like. The image display unit 1007, which is constituted by a liquid crystal panel and a touch sensor, for example, displays not only X-ray photographic images but also displays operation of the X-ray imaging apparatus, image size changing setting, a message, and a sequence status. That is, the image display unit 1007 also performs display of the operator console of the X-ray imaging control unit 1006.

The X-ray generator control unit 1001 applies a high voltage to the X-ray tube 1000 to generate an X-ray in accordance with photography conditions, such as a tube current value, a tube voltage, and an exposure time, provided by the operator console (not shown) or the X-ray imaging control unit 1006. The X-ray detection unit 1003 is constituted by an X-ray detector to detect an X-ray to obtain a digital image, an AEC unit used to minimize exposure of a human body to radiation and to suitably radiate an X-ray at a radiation dose required by the imaging apparatus, a grid to remove scattered radiation, and an A/D converter. It should be noted that the flat-panel sensor according to this embodiment provided to the X-ray detector is constituted by a scintillator that converts an X-ray to light and solid-state imaging devices that generate an electric signal corresponding to light intensity.

Of the X-ray incident from the X-ray tube 1000, X-rays scattered by the subject 1004 are removed by the grid of the X-ray detection unit 1003. The X-ray having passed through the grid is converted to light by the scintillator, following which an electric signal corresponding to the intensity of the light is generated by the solid-state imaging devices. The generated electric signal is converted into a digital value by the A/D converter, whereby a digital X-ray image is obtained. The AEC unit, which is placed between the grid and the X-ray detector, detects a part of the radiation having passed through the subject 1004 and the grid to generate an AEC signal, after which the AEC signal is transferred to the X-ray generator control unit 1001. The X-ray generator control unit 1001 integrates the values of the transferred AEC signals, and halts the transfer of the radiation generation signal when the integrated value has exceeded a threshold value, whereby the generation of the radiation at the X-ray tube 1000 is halted. Through such an operation, the AEC unit suitably adjusts the dose of radiation.

To the network 110, a HIS (hospital information system), a RIS (radiology information system), and a PACS (picture archiving and communication system) are connected. An X-ray image obtained by X-ray photography is output to the printer 1008 and the storage 1009 both connected to the network 110. And further, to the network 110, a diagnostic image processing workstation 1010 and a high-definition monitor 1011 are also connected. Moreover, in the diagnostic image processing workstation 1010, an application for image diagnoses by doctors called an image viewer is installed.

Figure 2B:
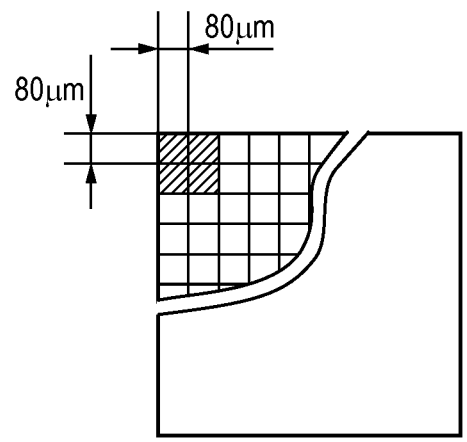

FIGS. 2A and 2B are explanatory drawings of a life-size output in which an X-ray photographic image is output in full size. The following is a description of a life-size output under conditions presented below at the flat-panel sensor (hereinafter referred to as "sensor") of the X-ray detection unit 1003 and the printer 1008.

Pixel Pitch at Sensor: 160 µm (FIG. 2A)
Number of Effective Sensor Pixels: 2688×2688 (FIG. 2A)
Pixel Pitch at Printer: 80 µm (FIG. 2B)
Number of Effective Printer Pixels: 4268×5108 (FIG. 2B)

When four pixels of the printer 1008 have been brought into correspondence with one pixel of the sensor, the total size of the pixels of the printer 1008 agrees with the size of the pixel of the sensor, and therefore the printer 1008 can output an image on the sensor in life size. Like this, when the sensor pixel pitch is an integral multiple of the printer pixel pitch, images can be correctly output in full size; in contrast, when the above relationship between both the pixel pitches is not brought about, no image is output in full size. For example, in a case where the printer pixel pitch is 78 µm, by bringing four printer pixels into correspondence with one sensor pixel, images are displayed in a size smaller than their full size by about 5% ($100-78^2/80^2\times100=4.94$). Even such a case is called "life-size image output" in the medical field, because it is important to display all image data representing a desired region detected by the sensor without any lack.

Figure 3:
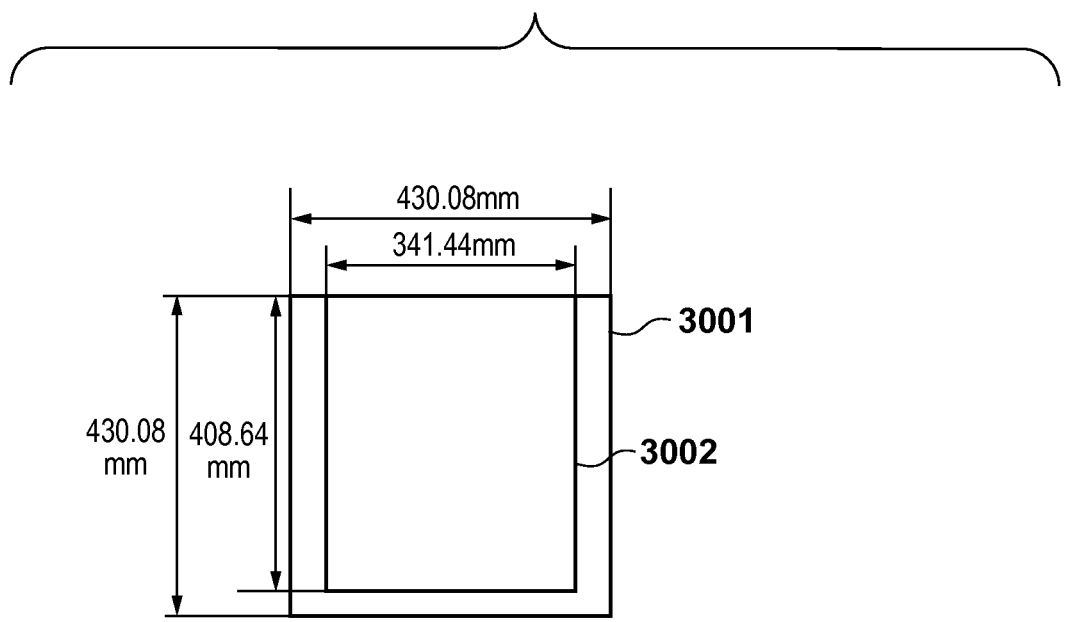
FIG. 3 is an illustration showing a relationship in effective size between a sensor and a printer.

FIG. 3 is an illustration showing a relationship in effective size between the sensor and the printer 1008. An effective size 3001 at the sensor refers to the size of an effective pixel region of the sensor, and an effective size 3002 at the printer 1008 refers to the size of an effective pixel region of the printer 1008. The pixel pitch at the sensor is set at 160 µm, the number of the effective sensor pixels is set at 2688×2688, the pixel pitch at the printer 1008 is set at 80 µm, and the number of the effective printer pixels 1008 is set at 4268×5108. Each effective size at the sensor and the printer 1008 can be found by multiplying the pixel pitch and the number of the effective pixels.

Effective Size 3001 at Sensor: 430.08 mm×430.08 mm
Effective Size 3002 at Printer: 408.64 mm×341.44 mm In the above example, the effective size of the printer 1008 is smaller than the effective size of the sensor, and it is, therefore, difficult to output image data on the entire surface of the sensor at the printer in doing life-size output.

Figure 4:
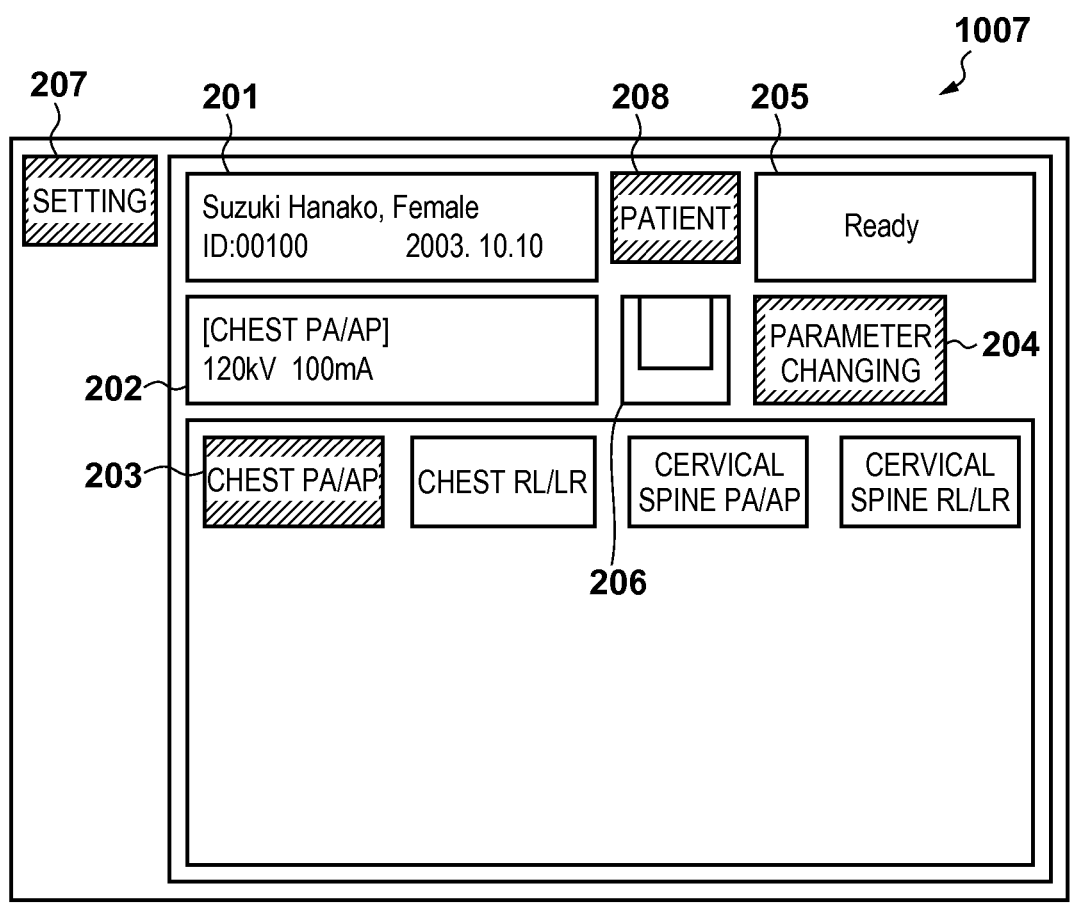
FIG. 4 is an illustration of an example of an imaging preparation screen.

FIG. 4 is an illustration showing an example of a screen on which a preparation for X-ray imaging is made displayed at the image display unit 1007. In FIG. 4, a patient data display box 201 is a region in which patient data, such as a patient's full name, ID number, sex distinction, and birth date, are displayed. An imaging condition display box 202 is a region in which imaging conditions, such as a tube current value, a voltage, an exposure time, and a patient-to-tube distance, are displayed. When a patient button 208 has been pressed, a patient data input window (not shown) is called up, and patient data are input via the input window. The imaging conditions are preset for each imaging method, and are automatically set by pressing an imaging method selection button 203.

The imaging method selection buttons 203 are buttons each used to maintain the status of an imaging operation; once any one of the buttons 203 has been pressed, the button 203 remains in a state of being depressed until the pressing is canceled, whereby it can be seen that which imaging method has been selected. In FIG. 4, "chest PA/AP" is selected. Note that this figure indicates that "chest PA/AP", "chest RL/LR", "cervical spine PA/AP", or "cervical spine RL/LR" can be selected by way of example, but the imaging methods according to the embodiment are not limited to those methods. And further, an operator cannot only register another imaging method such as "abdomen PA/AP", but delete data on the imaging method(s) that is not used. Moreover, for each imaging method selection button 203 are preset imaging conditions at imaging portions, AEC region setting, image processing parameters, correction processing setting, and the extraction position used when an image size is larger than an output size depending on an output medium. Furthermore, setting of the X-ray generator control unit including an aperture and a focal distance, setting of extraction positions (described below) determined in cases where an image size is larger than an image output size depending on the output medium, etc. are also made in advance for each imaging method selection button 203 (i.e., each imaging portion).

Figure 8:
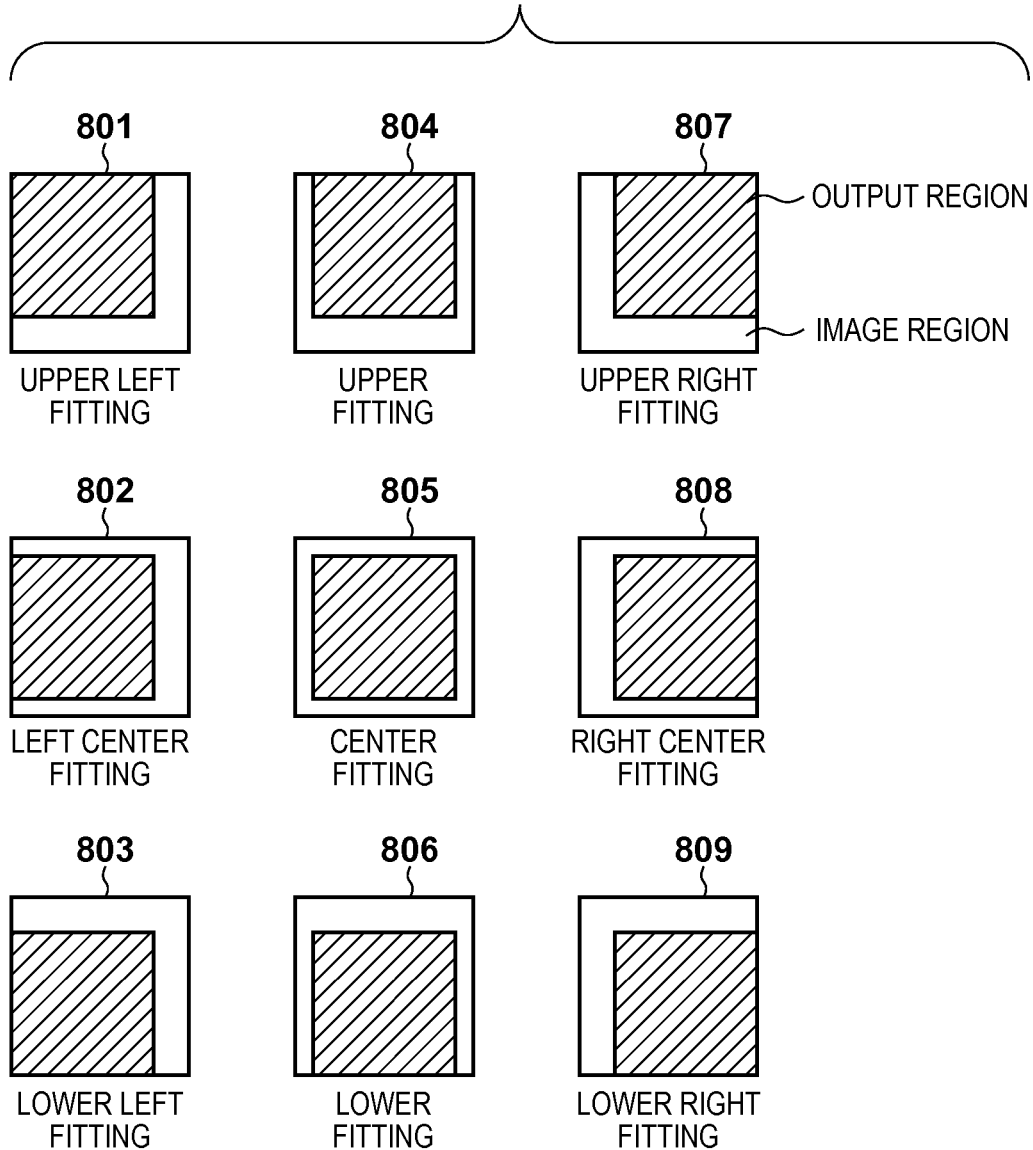
FIG. 8 is an explanatory drawing of image extraction positions.

A parameter changing button 204 is a button used to call up a window for changing parameters set via a selected imaging method selection button 203. In a status-message display box 205, a message and a status of the system are displayed (in FIG. 4, a "ready" status is displayed). When the size of an exposure field image or of an image extracted by an operator is larger than an image output size depending on the output device or the output medium, an extraction position box 206 shows the status of setting the extraction position for determining which region should be extracted from the image. The extraction position indicates a relationship in relative position between the entire region of an image and a region to be extracted from the image; in this embodiment, as shown in FIG. 8, nine extraction positions are set that are represented as upper left fitting 801, left center fitting 802, lower left fitting 803, upper fitting 804, center fitting 805, lower fitting 806, upper right fitting 807, right center fitting 808, and lower right fitting 809. FIG. 8 is an illustration showing extraction position setting that indicates the region to be extracted from the image when the size of an exposure field image or of an image extracted by an operator is larger than an image output size depending on the output device or the output medium.

The extraction positions shown in FIG. 8 are as follows:
Upper Left Fitting 801: the output region is fitted to the image region at the upper left corner.
Upper Fitting 804: the output region is fitted to the image region at the center in the upper end.
Upper Right Fitting 807: the output region is fitted to the image region at the upper right corner.
Left Center Fitting 802: the output region is fitted to the image region at the center in the left end.
Center Fitting 805: the output region is fitted to the image region at the center.
Right Center Fitting 808: the output region is fitted to the image region at the center in the right end.
Lower Left Fitting 803: the output region is fitted to the image region at the lower left corner.
Lower Fitting 806: the output region is fitted to the image region at the center in the lower end.

Lower Right Fitting 809: the output region is fitted to the image region at the lower right corner.

Since X-ray photography is generally done such that an object portion is positioned in the center of a radiographic table, "Center Fitting 805" is selected at the time of most X-ray photography. However, in cases where X-ray photography is performed with a subject's chin set on a chin pad placed at a relatively high portion of an X-ray apparatus like standing chest X-ray photography, for example, it is preferable to select "Upper Fitting 804", because a reference side of each X-ray image is set at the upper side of the image and many lesions are developed at lungs immediately under shoulders. Further, in cases where positioning of an object portion can be performed only at an end portion of a radiographic table in accordance with a patient's condition, upper left fitting 801, left center fitting 802, lower left fitting 803, upper right fitting 807, right center fitting 808, or lower right fitting 809 is suitably selected. Moreover, there are cases where positioning is limited to be at end portions depending on the installation location of an X-ray apparatus. In that case as well, upper left fitting 801, left center fitting 802, lower left fitting 803, upper right fitting 807, right center fitting 808, or lower right fitting 809 can be selected. Therefore a patient's condition button and an apparatus installation location button can be provided to change the extraction positions.

In cases where only the size in the height direction of an exposure field image or an image extracted by an operator is larger than that of a film, the left fitting, the right fitting, and the central fitting refer to the same formation in each of the upper end, the center and the lower end. In a case where each extraction position used when an image size is larger than a film size is preset at the imaging method selection button 203, a set value representing the extraction position is used. In contrast, in a case where the above presetting is not made, a value (i.e., an extraction position) set at the printer with an extraction position setting button 304 of FIG. 5 is used. A setting window calling button 207 is a button for calling up various setting windows.

FIG. 5 is an illustration of a setting window that is called up by pressing the setting window calling button 207, that is, a screen for inputting the size of an output medium. The left half of the window is a setting screen for the printer, and the right half is a setting screen for the storage. On the setting screen for the printer, a pixel pitch and an effective film size can be inputted in units of the number of pixels. By switching a printer tub 301, a plurality of printer settings can be made. A pitch between printer pixels is inputted in units of the number of pixels in order of width to length via a pixel pitch input box 302, and an effective film size is inputted in units of the number of pixels in order of width to length via a film size input box 303. And further, an extraction position used when an image size has exceeded a film size (an output region set at the printer) is set using the extraction position setting button 304. The extraction position setting button 304 is a toggle button; image fitting patterns corresponding to the nine extraction positions shown in FIG. 8 are set in order each time the extraction position setting button 304 is pressed. Alternatively, a setting dialog for selecting one of the nine patterns shown in FIG. 8 may be opened by pressing the extraction position setting button 304 to enable an extraction position setting. Values set on the window of FIG. 5 are default values determined in a case where an extraction position (an extraction position determined when an image size is larger than a film size) is not preset on the imaging method selection button 203.

In the first embodiment, the pixel pitch at the printer 1008 is 80 μm and the number of the effective pixels is 4268×5108 as described above, and thus settings shown in FIG. 5 is made. And further, since image sizes to be stored into the storage 1009 are not limited in the first embodiment, a maximum image output size is determined based on the number of the effective sensor pixels. Since the number of the effective sensor pixels is 2688×2688 and the pixel pitch at the sensor is 160 μm, data denoted by reference numeral 305 in FIG. 5 is displayed. An OK button 306 is a button used to confirm such various settings, and a cancel button 307 is a button used to cancel those settings.

Figure 6:
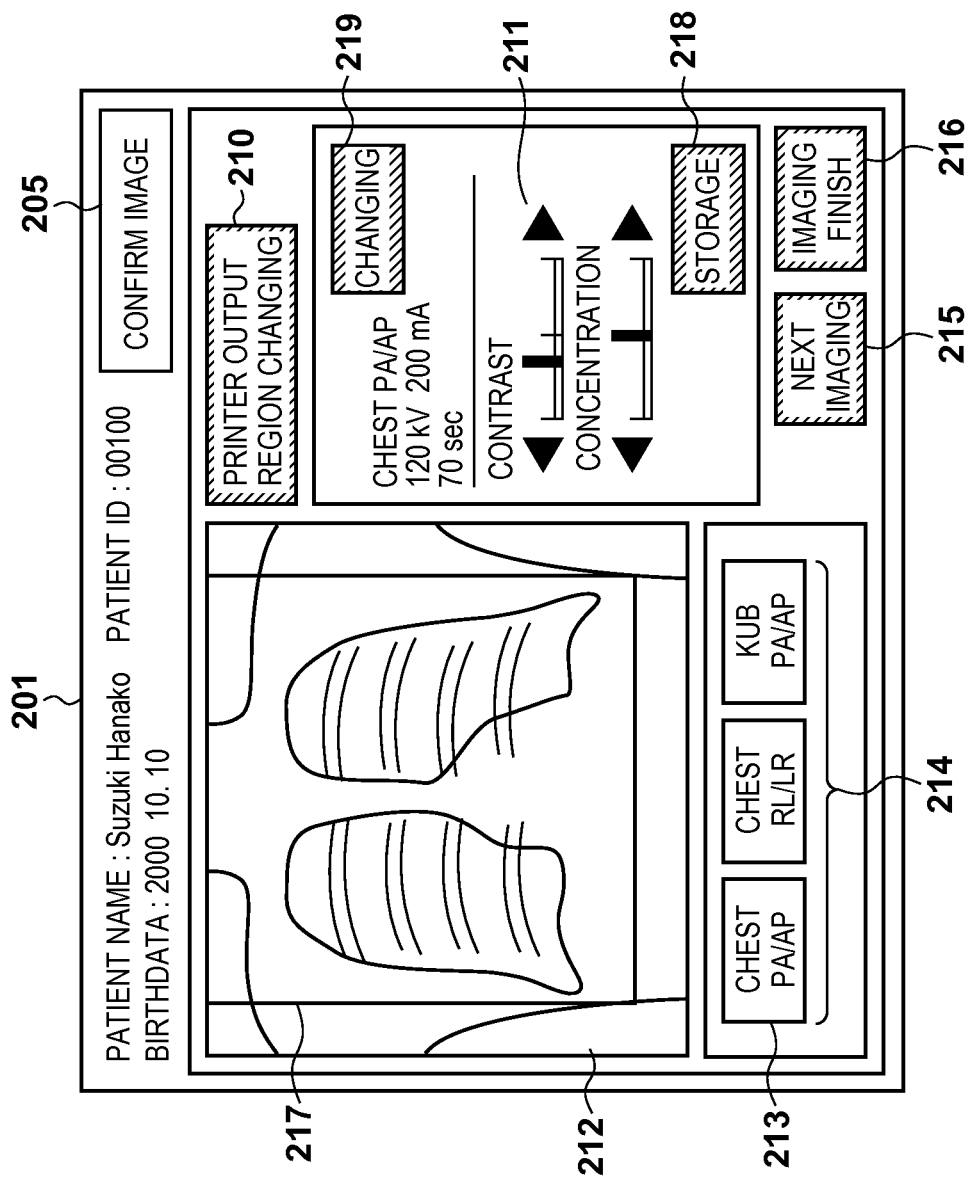
FIG. 6 is an illustration of an example of a storage output region changing screen.

FIG. 6 is an illustration of a screen at the image display unit 1007 on which an X-ray photographic image 212 is displayed. A storage output region 217 in the X-ray photographic image 212 refers to an output region for an output to the storage 1009, which represents a region equal to an exposure field immediately after X-ray irradiation. By clicking an upper left portion and a lower right portion of a desired region in the X-ray photographic image 212, an operator can change the storage output region 217. And further, it is also possible to shift the storage output region 217 while maintaining the size of the region 217. The change of the storage output region 217 is accepted by pressing a storage button 218, whereby the storage output region 217 is updated. It should be noted that it is apparent that a method for accepting the change of the storage output region 217 is not limited to such a manipulation. In addition, when changing the printer output region 217, a screen of FIG. 7 is called up by pressing a button 210, on which the change is made.

Figure 7:
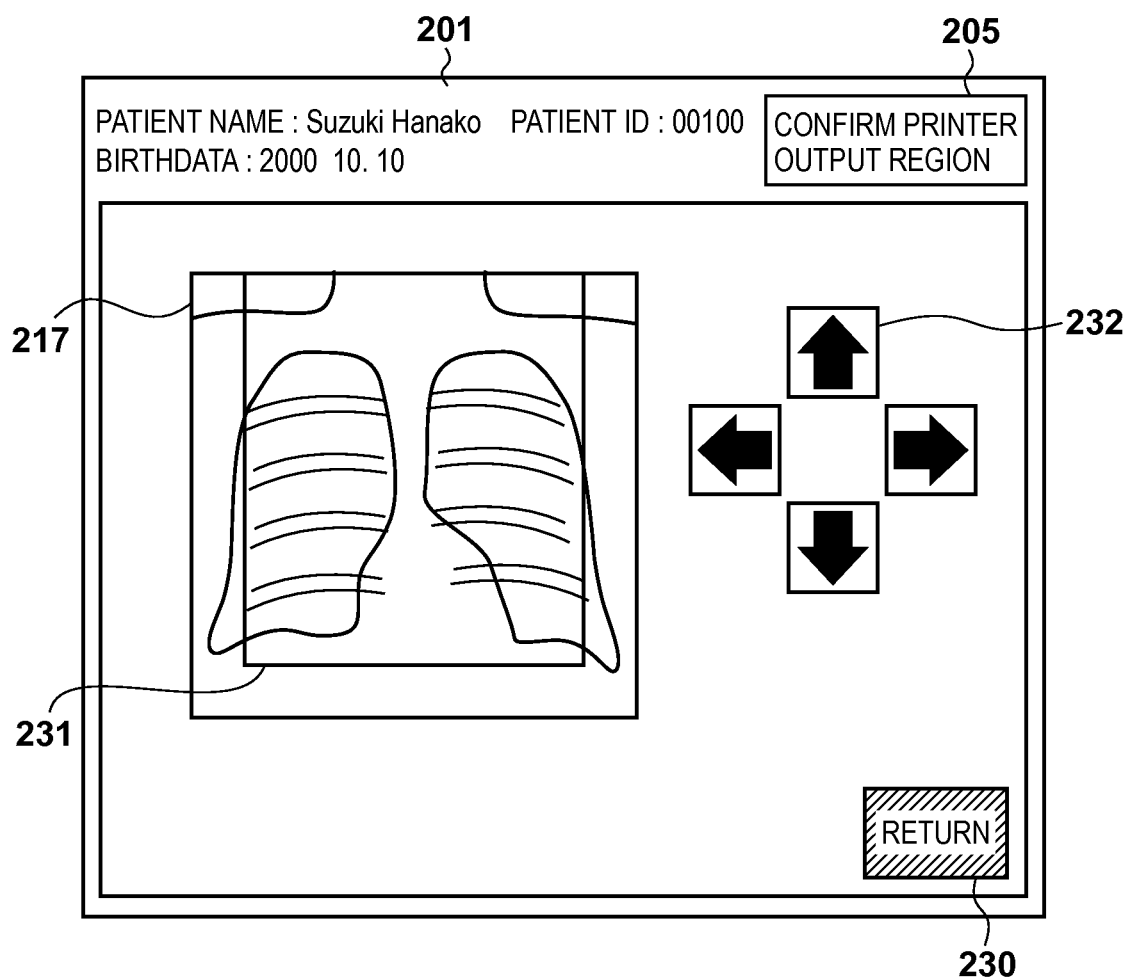
FIG. 7 is an illustration of an example of a printer output region changing screen.

FIG. 7 is an illustration of a printer output region changing screen displayed at the image display unit 1007. In FIG. 7, a printer output region 231 is shown within the storage output region 217. And further, the printer output region 231 can be shifted by using a frame shift key(s) 232, and the printer output region 231 also can be changed by clicking an upper left portion and a lower right portion of a desired region in the storage output region, but cannot be changed beyond the storage output region. Moreover, the maximum size of the printer output region 231 is a film size for image output, and it may be, therefore, impossible to set the printer output region 231 larger the film size.

By pressing a return button 230 of FIG. 7, a return to the image display in FIG. 6 is made. An image manipulation section 211 is a user interface used to adjust a contrast and a concentration in the X-ray photographic image 212. By pressing a changing button 219, parameters of the adjusted contrast and concentration are stored, and these parameters are further applied to other images. At an imaging method display section 214, the imaging method selected via the imaging method selection button 203 ("chest PA/AP 213" in FIG. 6) is displayed distinguishably to an operator. By pressing a next imaging button 215, a standby status is brought about for the next imaging. By pressing an imaging finish button 216, the series of imaging operations are finished.

Figure 9:
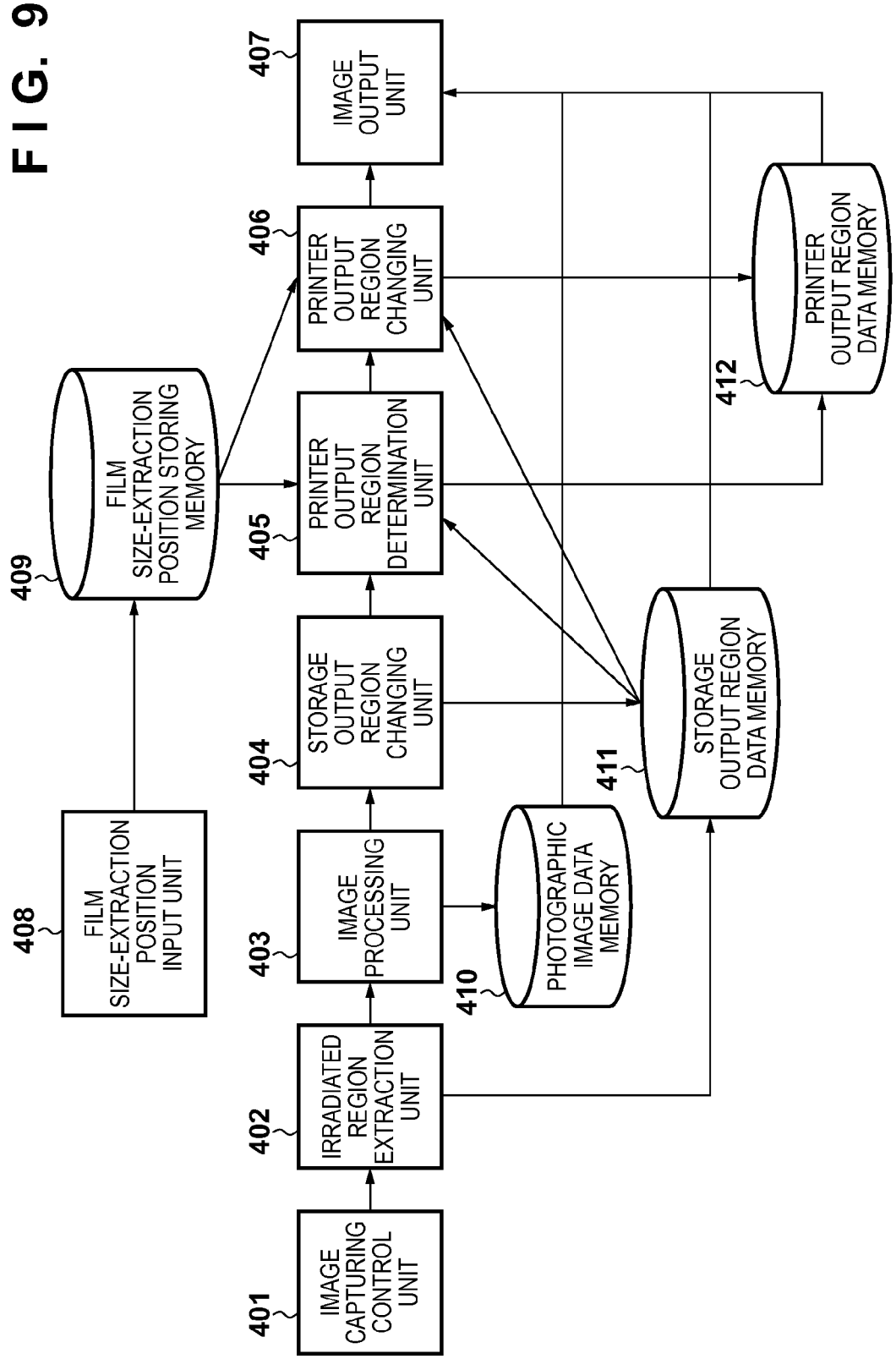
FIG. 9 is a block diagram of a configuration example of an X-ray imaging apparatus according to the first embodiment.

FIG. 9 is a block diagram of the X-ray imaging control unit 1006 of the digital X-ray imaging system according to the first embodiment. After X-ray exposure, an image capturing control unit 401 obtains digital data on the entire effective pixel region from the X-ray detection unit 1003, or may obtain, from a storage medium such as a hard disk, digital image data on an effective pixel region already obtained from the X-ray detection unit 1003. And further, the image capturing control unit 401 performs various kinds of correction processing.

Next, an irradiated region extraction unit 402 extracts a region extracted by the exposure field aperture 1002 from the digital image obtained at the image capturing control unit 401, following which the coordinates of the region are stored in a storage output region data memory 411. As a method for recognizing an exposure field, an exposure field may be obtained based on the extraction amount of an image region at the exposure field aperture 1002, or an exposure field may be recognized by analyzing a digital image through the use of a known technique described in Japanese Patent Laid-Open No. 2001-307064, for example.

Then predetermined image processing is performed at an image processing unit 403, and the processed image data is stored in a photographic image data memory 410. Examples of the above image processing include gradation processing and frequency processing that are suitable for observations by doctors. Next, the size of an effective pixel region in a film used and the resolution of the printer shown in FIGS. 4 and 5 and the extraction position selected from the nine extraction positions shown in FIG. 8 are input into a film size-extraction position input unit 408. It should be noted that although the size of the film's effective pixel region and the printer's resolution are manually input using the user interface of FIGS. 4 and 5 in this embodiment, the input medium according to this embodiment is not limited to such a medium. For example, data on a film's effective pixel region and the printer's resolution may be automatically obtained from the printer 1008 online via the network 110. Moreover, as shown in FIG. 5, a plurality of film sizes can be set. When a plurality of film sizes are set, a film size preset with respect to a designated imaging method (for example, "chest PA/AP") or a film size closest to the preset film size is used as an output region at the printer 1008. Alternatively, of the plurality of film sizes already set, a maximum film size is used as an output region at the printer. The film size-extraction position input unit 408 causes a film size-extraction position storing memory 409 to store the input film size and extraction position.

At a storage output region changing unit 404, the storage output region 217 is changed on the screen of FIG. 6, following which the coordinates of the changed storage output region 217 are stored in the storage output region data memory 411. A printer output region determination unit 405 compares the storage output region 217 and the film size. When the storage output region 217 is larger, the printer output region determination unit 405 extracts a film output region from the storage output region by using one of the extraction positions stored in the film size-extraction position storing memory 409. Thereafter, the printer output region determination unit 405 causes a printer output region data memory 412 to store the coordinates of the extracted film output region. A printer output region changing unit 406 changes the printer output region 231 on the printer output region changing screen of FIG. 7. The coordinates of the changed printer output region 231 are stored in the printer output region data memory 412. Then an image output unit 407 generates an image by using the photographic image data memory 410, the storage output region data memory 411, and the printer output region data memory 412, and then outputs the image to the storage 1009 and the printer 1008.

The X-ray photography process according to this embodiment will be described below with reference to FIGS. 1 to 9.

A medical X-ray technician or a doctor as an operator sets the size of an output medium before X-ray photography. The operator presses the setting window call button 207 on the imaging preparation screen of FIG. 4 to display the output size setting screen of FIG. 5. On the output size setting screen an extraction position is set which is used when an image size determined based on a film size for image output set at the printer and the printer pixel pitch has exceeded the film size. These set values are stored in the film size-extraction position storing memory 409. And further, an extraction position used when an image size has exceeded a film size is suitably set in advance for each imaging method selection button 203 on a parameter changing window (not shown) called up by pressing the parameter changing button 204 by the operator.

The medical X-ray technician or the doctor as the operator inputs patient data and determines an imaging method on the imaging preparation screen of FIG. 4. The patient data is input via a patient data input screen (not shown) called up by pressing the patient button 208. Alternatively, to increase efficiency in data entry operation and prevent false data entry, patient data may be input from a magnetic card or a bar code (both are not shown), or may be input from the hospital information system (HIS) or the radiology information system (RIS) via the network 110. The input patient data is displayed in the patient data display box 201.

Next, the operator pressed the desired imaging method selection button 203 on the imaging preparation screen (of FIG. 4) to set an imaging portion. In the example in FIG. 4, to X-ray the front of the chest, the imaging method selection button 203 represented as "Chest PA/AP" is pressed. By designating the imaging method selection button 203, various parameters are set such as imaging parameters, image processing parameters, correction processing parameters, parameters for generator setting, and preset values presenting the extraction position (any one of the extraction positions in FIG. 8) used when image sizes are larger than film sizes. Part of the imaging parameters is displayed in the imaging condition display box 202 of FIG. 4. Moreover, in the extraction position box 206 used when the image sizes are larger than the film sizes, the values preset at the imaging method selection button 203 are displayed, or values provided at the extraction position setting button 304 set on the setting screen of FIG. 5 are displayed when the above various parameters are not set.

By pressing the parameter changing button 204, the parameter changing window (not shown) is called up. On the parameter changing window, the preset parameters can be changed such as the imaging parameters, the image processing parameters, the correction processing parameters, the parameters for the generator setting, and the preset values representing the extraction position used when the image sizes are larger than the film sizes.

Then, by having a subject 1004 stand in front of the X-ray detection unit 1003 as shown in FIG. 1 and moving an elevating unit up or down through pressing of the seesaw pedal (not shown) of the elevating unit, positioning of the X-ray detection unit 1003 is performed such that the subject 1004 is suitably placed relative to the X-ray detection unit 1003. For example, with "Chest PA/AP" X-ray photography, a patient is firmly set by placing the patient's chin on a chin pad placed at the top end of the X-ray detection unit 1003. Then the X-ray tube 1000 is moved back and forth to change a distance between the patient and the X-ray tube 1000, and the exposure field aperture 1002 is adjusted so as not to irradiate body parts other than an object part with an X-ray.

After having made the above X-ray photography preparations, in the X-ray detection unit 1003 of FIG. 1, a voltage is applied to solid-state imaging devices included in the sensor of the X-ray detection unit 1003 based on a solid-state imaging device driving control signal from the X-ray imaging control unit 1006. This puts the solid-state imaging devices ready for receiving an image of the subject 1004 at any time. The various preset parameters corresponding to the imaging method selection buttons 203 (including the preset parameters changed on the parameter changing window) are transferred to the X-ray detection unit 1003, the X-ray imaging control unit 1006, and the X-ray generator control unit 1001. The transfer brings about a state in which X-ray photography can be performed using the parameters set with respect to the imaging method selected via the imaging method selection button 203.

Then an X-ray irradiation button placed near the image display unit 1007 is pressed by the operator. The irradiation button triggers the generation of an X-ray at the X-ray tube 1000; with pressing of the button by the operator, an irradiation signal is generated. The irradiation signal generated by the pressing of the irradiation button is temporarily send to the X-ray imaging control unit 1006. In response to this, the X-ray imaging control unit 1006 confirms whether the solid-state imaging devices are in a state of being able to perform imaging at the time of incidence of the X-ray from the X-ray tube 1000, based on a state of a drive notification signal generated by the solid-state imaging devices, and then generates an irradiation permission signal to an irradiation switch. The irradiation permission switch is turned on with the irradiation permission signal. When the irradiation permission switch has been turned on, the irradiation signal generated by pressing the second switch of the irradiation button is supplied to the X-ray generator control unit 1001.

The X-ray generator control unit 1001 transmits the irradiation signal to the X-ray tube 1000, whereby the X-ray tube 1000 generates an X-ray. At that time, irradiation conditions are presented based on the preset values provided when having pressed the imaging method selection button 203 or the values provided by changing the above preset values at the parameter changing window. The X-ray generator control unit 1001 radiates X-rays only for a time specified base on an appropriate irradiation time. However, the X-ray generator control unit 1001 halts the X-ray irradiation when the total quantity of X-ray dose signals added up after their capture from the AEC unit with respect to an selected AEC region has reached a predetermined certain quantity. In cases where an X-ray dose is controlled by an AEC device, an irradiation time presented as one of irradiation conditions (an irradiation time presented in the form of preset parameters) is increased in general.

The X-ray generated by the X-ray tube 1000 is confined by the exposure field aperture 1002, passes through the subject 1004, the grid (not shown), and the scintillator (not shown) in order, and is formed into a radiographic image of the subject 1004 at the solid-state imaging devices. Thereafter, the ray is photoelectrically converted into an image signal by the solid-state imaging devices. The image signal is digitized by the A/D converter, following which the resulting digital signal is input to the X-ray imaging control unit 1006.

Next, the irradiated region extraction unit 402 extracts the region confined by the exposure field aperture 1002 from the digital image obtained at the image capturing control unit 401, and the coordinates of the region are stored in the storage output region data memory 411. As a method for recognizing the exposure field, as described earlier, the exposure field may be recognized based on the quantity confined by the exposure field aperture 1002, or may be recognized using a known image analysis. In this embodiment, the coordinates representing a rectangular extracted as the irradiated region are stored in the storage output region data memory 411.

Then the image processing unit 403 performs various kinds of image process such as gradation processing and frequency processing that are suitable for observation by a doctor(s), following which the X-ray photographic image is displayed at the image display unit 1007, and is stored in the photographic image data memory 410. When necessary, the storage output region changing unit 404 receives data on the storage output region changed by the operator on the storage output region changing screen of FIG. 6. The storage output region changing unit 404 causes the storage output region data memory 411 to store the region of the extracted exposure field or the output region changed by the operator as the coordinates of the storage output region. Thereafter, the printer output region determination unit 405 compares the storage output region derived from the storage output region data memory 411 and the film size derived from the film size-extraction position storing memory 409. When the storage output region is smaller, the printer output region determination unit 405 causes the printer output region data memory 412 to store the coordinates of the storage output region. When the film size is smaller, the printer output region determination unit 405 derives the extraction position from the film size-extraction position storing memory 409, and extracts a region for the film size based on the extraction position set within the storage output region. Through such operations, a printer output region is determined, and then the printer output region data is stored in the printer output region data memory 412.

The printer output region changing unit 406 calls up a printer output region changing screen as shown in FIG. 7 so that the operator can change the printer output region 231 within the storage output region 217. Through a shift of the printer output region 231 using the frame shift key 232, designation of the region 231 using clicks on the upper left and lower right portions, or the like, the position and/or the size of the printer output region 231 are changed. At that time, when having designated the printer output region larger than the film size, a film-sized region is extracted at a set extraction position within the designated region, and is determined as the printer output region. After the determination of the printer output region, the printer output region changing unit 406 causes the printer output region data memory 412 to store the output coordinates of the printer output region. Through the above operation, the storage output region and the printer output region are suitably adjusted and stored. It should be noted that with the printer output region changing screen of FIG. 7, since the position of the printer output region 231 is limited within the storage output region 217, an outside of the exposure field and a region unrelated to the object portion are not extracted, and operation efficiency can, therefore, be enhanced.

After having performed all imaging in the same way, an imaging finish button 216 on the storage output region changing screen (FIG. 6) is pressed. At this time, the image output unit 407 generates an image for storage output from the X-ray photographic image held in the photographic image data memory 410 and the coordinates held in the storage output region data memory 411, and outputs the image for storage output to the storage 1009. At the same time, an image for printer output is generated from the X-ray photographic image held in the photographic image data memory 410 and the coordinates held in the printer output region data memory 412, and outputted to the printer 1008.

The X-ray image output processing by the X-ray imaging control unit 1006 according to this embodiment in which an optimum output region is set for each output destination as described above will be described below with reference to a flowchart of FIG. 10.

At steps S601 to S603, first determination processing is performed in which either an extracted irradiated region or a partial region selected from an X-ray photographic image by the user is set as an output region to the storage 1009. Initially, at step S601, the irradiated region extraction unit 402 extracts an irradiated region from an X-ray photographic image obtained by the image capturing control unit 401, and the coordinates of the irradiated region are stored in the storage output region data memory 411 as a storage output region.

Then, at step S602, the processing branches based on whether the storage output region is changed. When the storage output region has been changed on the storage output region changing screen of FIG. 6, the storage output region changing unit 404 changes the storage output region, and the coordinates of the changed output region are input to the storage output region data memory 411 (steps S602 and S603).

Next, at steps S604 to S608, second determination processing is performed in which an output region to the printer 1008 is determined. It should be noted that at the time of the start of the second determination processing, it is assumed that the above storage output region is held in the printer output region data memory 412. To begin with, at step S604, the printer output region determination unit 405 compares an output size found from the storage output region and a selected film size at the printer (the size of a printer output region). When the storage output region is not larger than the film size (the image size of the printer output region), the processing goes to step S609. In this case, the storage output region is used as the printer output region. In contrast, when the storage output region is larger than the film size, the processing shifts to step S606, at which the printer output region determination unit 405 extracts a region corresponding to the film size (the printer output region) from the extraction portion set within the storage output region. It should be noted that although the extraction position set for each imaging method is used at step S606, a film output region is determined based on the extraction position set via the output size setting screen of FIG. 5 when the setting for each imaging method is not made. And further, when the extraction position is set at "Upper Fitting", a printer output region is determined by fitting the centers in the upper ends of the storage output region and a frame corresponding to the film size to each other. Moreover, when the extraction position is set at "Lower Left Fitting", a printer output region is determined by fitting the lower left corners of the storage output region and a frame corresponding to the film size to each other. In the other seven fitting patterns as well, individual printer output regions can be determined in the same way.

Then, at step S607, the processing branches based on whether the printer output region is changed. When the button 210 of FIG. 6 has been pressed, the processing shifts from step S607 to step S608 to change the printer output region. At step S608, the printer output region changing unit 406 causes the image display unit 1007 to display the printer output region changing screen of FIG. 7, and receives the change of the output region by the operator. Thereafter, the printer output region changing unit 406 causes the printer output region data memory 412 to store the coordinates of the output region presented by the operator.

When the imaging finish button 216 in the screen of FIG. 6 has been pressed, the processing goes to step S609. The X-ray imaging control unit 1006 obtains the X-ray photographic image from the photographic image data memory 410, obtains the storage output region from the storage output region data memory 411, obtains the printer output region from the printer output region data memory 412, generates an image for storage output and an image for printer output, and then outputs both the above images. When the set printer output region is smaller than the film size at that time, the image within the printer output region is positioned in the center of the film. By executing the above procedure every time, all X-ray photographic images are outputted in sizes corresponding to the parameters set at the storage and the printer.

When the next imaging button 215 in the screen of FIG. 6 has been pressed, the above processing from the obtainment of the X-ray photographic image to the image output processing (steps S601 to S609) is repeated. And further, in the flowchart of FIG. 10, although a printer output region is not adjusted when a printer output size (a maximum size of a set film) is larger than a storage output region, there is no limitation to this. For example, a method may be used in which even when a printer output size is larger than a storage output region, a printer output region can be adjusted.

Although the number of the connected printer 1008 is one and the number of the kind of film is also one in the above example, the foregoing effect can also be obtained in a case where a plurality of printers are connected thereto or in a case where an image is simultaneously output to a plurality of films. In that case, a method can be used in which a tub for switching between the printers and a tub for switching between the films are provided in the printer output region changing screen of FIG. 7 so that a printer output region can be set at each printer. And further, the printer output region data memory 412 becomes easier to manage by providing the memory 412 with a two-dimensional structure composed of a printer-side storage area and a film-side storage area.

Figure 11:
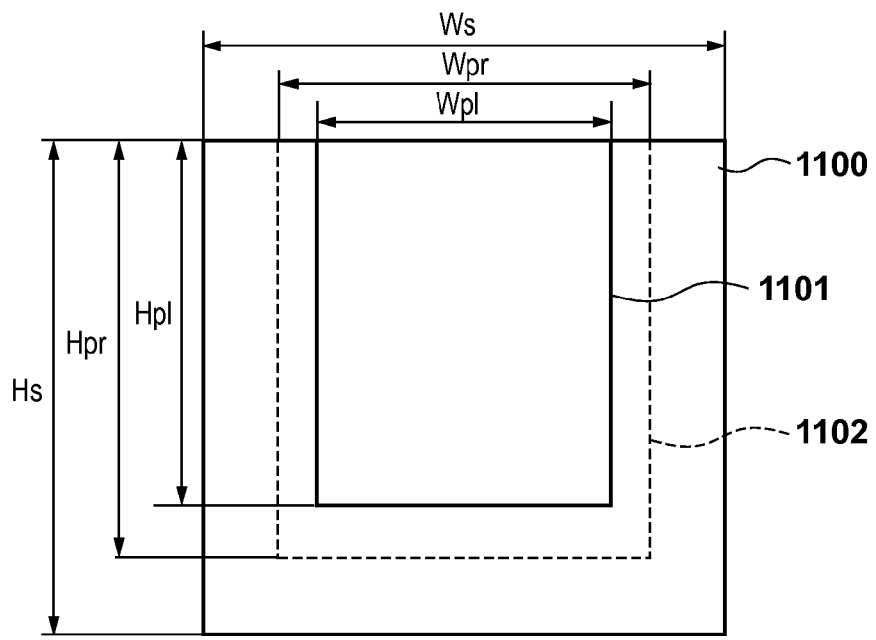
FIG. 11 is an explanatory drawing showing a relationship between an effective size at the sensor, film size given in life size, and a film size at a predetermined reduction ratio.

In this embodiment, as in the case of the above assumption that life-size printing is performed, the foregoing effect can be obtained even in a case where an image is output at a predetermined reduction ratio. With regard to image output done at such a reduction ratio, FIG. 11 shows a relationship between an effective size 1100 at the sensor, a film size (output medium size) 1101 given in life size, and a film size (output medium size) 1102 at a predetermined reduction ratio. The above relationship is expressed by Expression (1) given below.

$$Wpl = K \times Wpr$$

$$Hpl = K \times Hpr \quad (1)$$

where "Wpl and Hpl" are an output medium size 1101 for life-size output, and "Wpr and Hpr" are an output medium size 1102 for output at the predetermined reduction ratio.

By using Expression (1), an output medium size 1102 (Wpr and Hpr) at a reduction ratio is found. In the first embodiment, by replacing the output medium size 1101 (Wpl and Hpl) given in life size by the output medium size 1102 (Wpr and Hpr) for output at the predetermined reduction ratio, the foregoing effect can be obtained. It should be noted that the proportionality constant k in Expression (1) is given as follows:

$$K = \sqrt{(R/100)} \quad (2)$$

where R(%) is an area reduction ratio.

Second Embodiment

Figure 12:
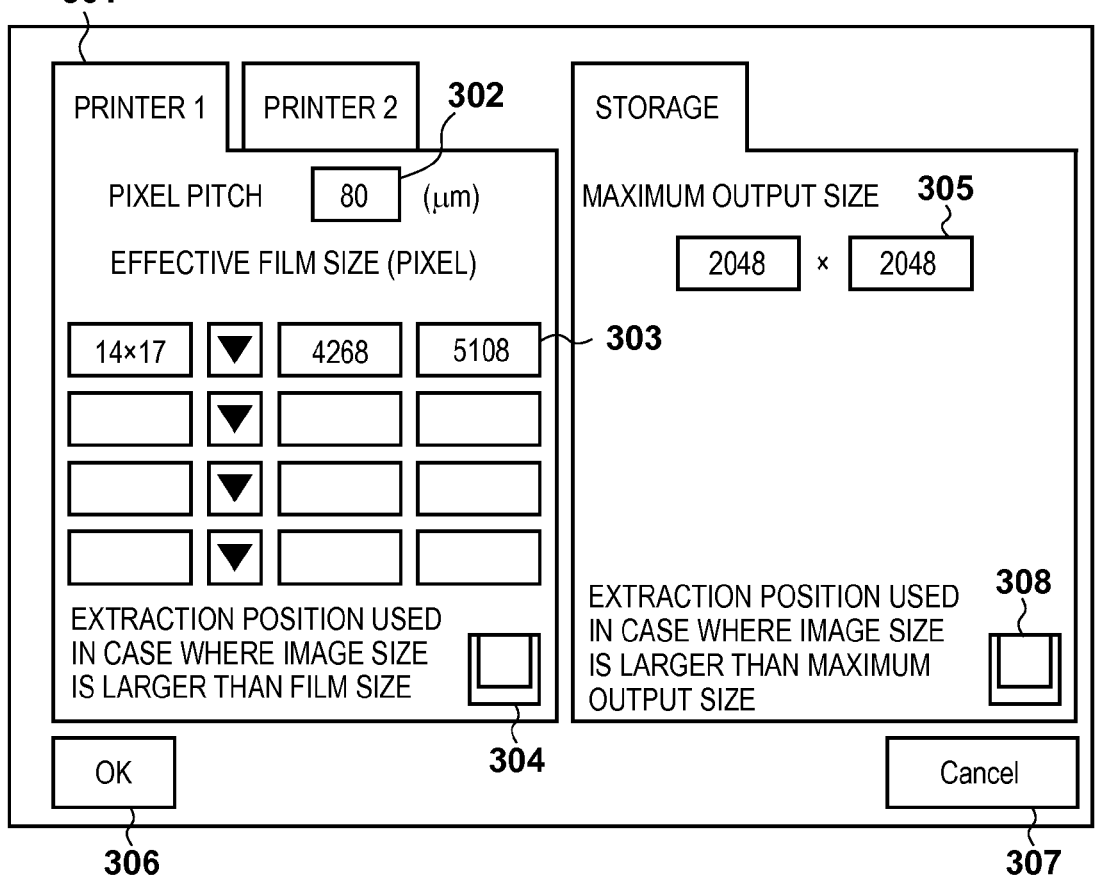
FIG. 12 is an illustration of an example of an output size setting screen according to the second embodiment.
Figure 13:
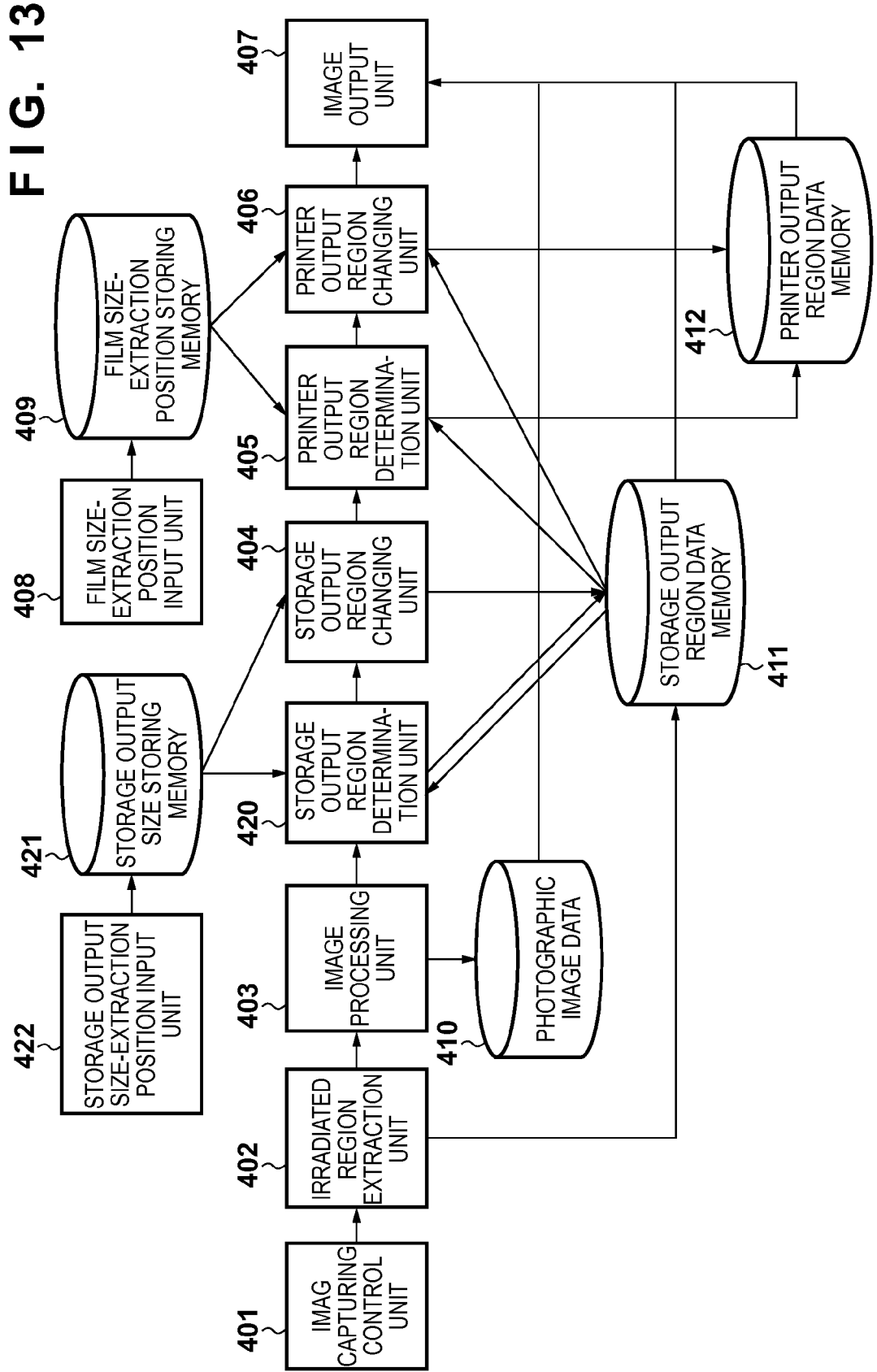
FIG. 13 is a block diagram of a configuration example of an X-ray imaging apparatus according to the second embodiment.

A second embodiment of the present invention will be described below with reference to the output size setting screen shown in FIG. 12, the block diagram according to the second embodiment shown in FIG. 13, and the flowchart according to the second embodiment shown in FIG. 14.

Although the sizes of images transferred to the storage are not limited in the first embodiment, image sizes that can be used at commercially available image viewers are often limited in actuality. Since there are many cases where a maximum image size is limited in particular, the second embodiment provides a method of making an operator set a maximum output size of a storage output region on the output size setting screen of FIG. 12. In this embodiment, a setting is shown that is made in a case where a maximum image size that can be used at the diagnostic viewer is set at 2048×2048 pixels. And further, the individual extraction sizes may be preset for each imaging portion. Moreover, in a case where the above presetting is not made for each imaging portion, the maximum output size set on the output size setting screen of FIG. 12 may be used as a storage output size. Furthermore, when an image size is larger than a maximum size of a set storage output region, the extraction position of the storage output region can be set by using an extraction position setting button 308. The extraction position is selected by using the same method as that used in the first embodiment (see FIG. 8). The set maximum size of the storage output region and the set extraction position are inputted by a storage output size-extraction position input unit 422, and stored in a storage output size storing memory 421.

Figure 14:
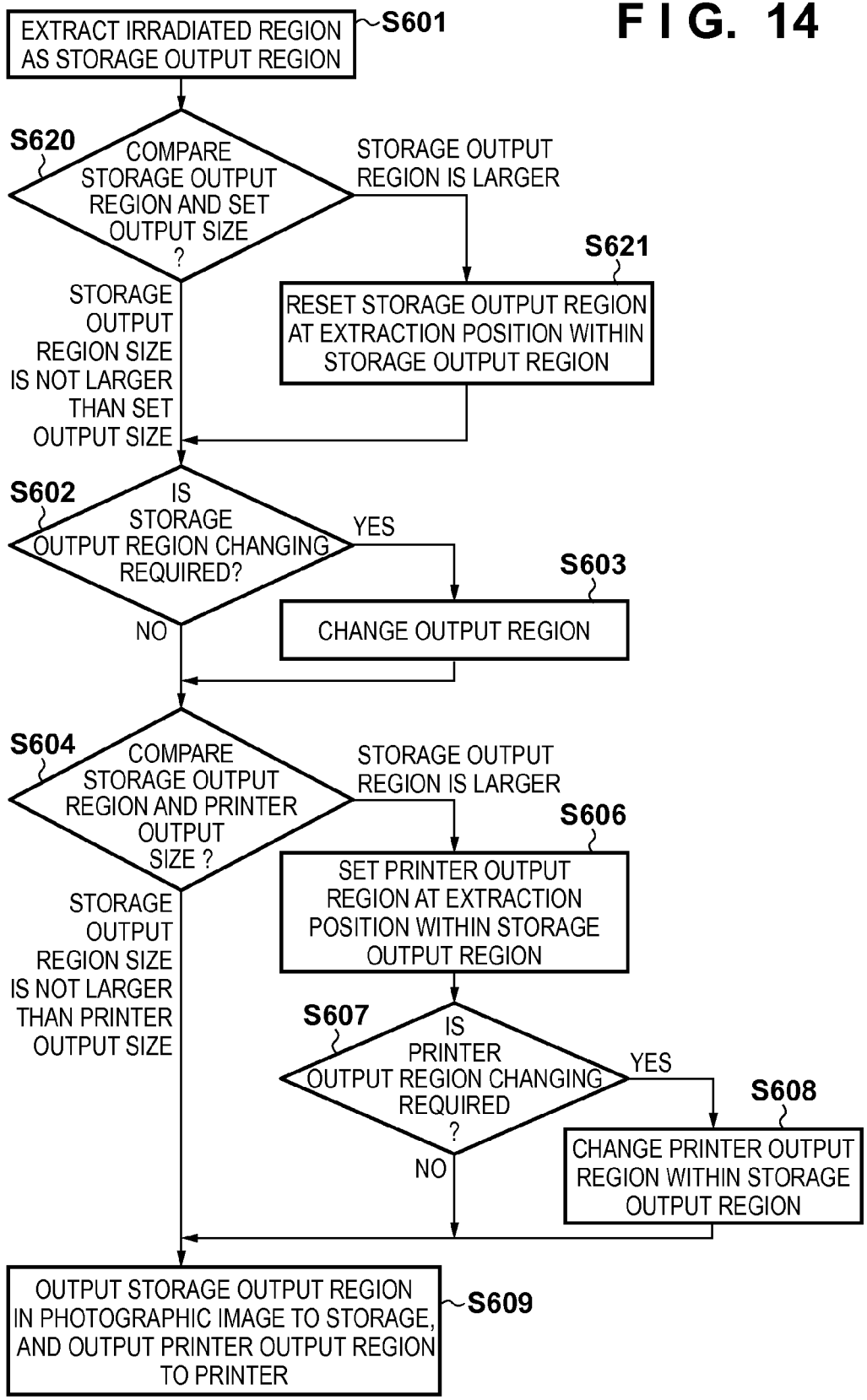
FIG. 14 is a flowchart of a procedure of image output region determination processing according to the second embodiment.

In the second embodiment, the first determination processing is modified as shown in steps S601, S620, S621, S602, and S603 in the flowchart of FIG. 14. That is, to begin with, at step S601, the irradiated region extraction unit 402 extracts the irradiated region of an X-ray photographic image, and causes the storage output region data memory 411 to store the coordinates of the irradiated region as a storage output region. Next, at step S620, a storage output region determination unit 420 compares the storage output region stored in the storage output region data memory 411 and a set storage output size stored in the storage output size storing memory 421. When the storage output region is larger, the processing goes to step S621. At step S621, the storage output region determination unit 420 extracts a region of a set storage output size from the storage output region. At step S621, a region of the storage output size is extracted from the storage output region at the extraction position set at the extraction position setting button 308, following which the extracted region of the storage output size is stored in the storage output region data memory 411 as another storage output region. When the size of the storage output region is not larger than the set output size, the entire region of the extracted irradiated region is used as the storage output region.

The storage output region changing unit 404 performs processing at steps S602 and S603, which are basically the same as steps S602 and S603 described in the first embodiment. However, in storage output region changing operation performed on the storage output region changing screen of FIG. 6, every time a region has been designated by clicking two opposite points such as upper left and lower right points, it is determined whether the designated region is smaller than the set storage outside size stored in the storage outside size storing memory 421. If the designated region is larger than a set storage output size, a region of a storage output size is extracted at the extraction position set via the extraction position setting button 308 within the designated region, and the extracted region is set as another storage output region. The storage output region thus determined is stored in the storage output region data memory 411.

The printer output region determination unit 405 performs processing at steps S604 and S606, the printer output region changing unit 406 performs processing at steps S607 and S608, and the image output unit 407 performs processing at step S609; however, each processing described above is the same as that described in the first embodiment, and their description will, therefore, be omitted.

As described above, according to the above embodiments, even in the case where output sizes at a storage are determined, setting of an optimum-size image region can be effectively made at a storage and a printer. That is, an optimum extraction at a storage and a printer can be made with easy operation without extracting any outside of an exposure field and any unrelated region.

According to the present invention, operability, when outputting an X-ray image to a plurality of output apparatuses having different suitable output sizes, is improved.

While the present invention has been described above with reference to the preferred embodiments, it is to be understood that the invention is not limited to the disclosed exemplary embodiments, and various modifications and changes can be made within the sprit and the scope of the invention.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An information processing apparatus that transfers an X-ray image to a plurality of output apparatuses each of which outputs an X-ray image, said information processing apparatus comprising:
   a region obtaining unit configured to obtain an irradiated region on an X-ray image obtained by X-ray imaging;
   an information obtaining unit configured to obtain information indicating allowable output size for each of a first output apparatus and a second output apparatus whose allowable output sizes are different from each other; and
   a transferring unit configured to transfer a first image to the first output apparatus, which is obtained by extracting at least a portion of the X-ray image based on the irradiated region and allowable output size of the first output apparatus, and transfer a second image to the second output apparatus, which is obtained by extracting at least a portion of the first image based on an allowable output size of the second apparatus.

2. The apparatus according to claim 1, wherein said transferring unit is configured to transfer the first image to an external storage apparatus.

3. The apparatus according to claim 2, wherein said transferring unit is configured to transfer images to a storage apparatus for outputting an image to a display unit as the external storage apparatus.

4. The apparatus according to claim 1, wherein said transferring unit is configured to transfer the second image to a printer.

5. The apparatus according to claim 1, further comprising a first selecting unit configured to causing a user to select a position for extracting the first image from the irradiated region.

6. The apparatus according to claim 1, further comprising a second selecting unit configured to select a position for extracting the second image from the first image.

7. The apparatus according to claim 1, further comprising a designation unit configure to designate an imaging portion for X-ray imaging, wherein, in said transferring unit, a position for extracting the first image from the irradiated region is determined based on the imaging portion designated by said designation unit.

8. The apparatus according to claim 1, further comprising a designation unit configure to designate an imaging portion for X-ray imaging,
wherein a position for extracting the second image from the first image is determined based on the imaging portion designated by said designation unit.

9. The apparatus according to claim 1, wherein said transferring unit is configured to transfer an image obtained by extracting a portion of the first image as the second image in a case where a size of the first image is larger than the allowable output size of the second output apparatus, and to transfer the first image as the second image in a case where the size of the first image is not larger than the allowable output size of the second output apparatus.

10. The apparatus according to claim 1, wherein the first irradiated region is used as the first image in a case where the irradiated region has a size that is not larger than the allowable output size of the first output apparatus.

11. The apparatus according to claim 1, wherein said transferring unit is configured to extract the first image based on an image region designated by a user's operation input though an operating unit.

12. The apparatus according to claim 1, wherein a size of the first image is determined based on a pixel size in the X-ray image and number of pixels in the first image.

13. The apparatus according to claim 12, wherein the size of the first image is determined by multiplying a predetermined reduction ratio by a size obtained based on the pixel size and the number of pixels.

14. The apparatus according to claim 1, wherein the first output apparatus comprises a storage apparatus that is connected to the information processing apparatus through a communication network, and the second output apparatus comprises a printer.

15. An information processing apparatus that transfers an X-ray image to a plurality of output apparatuses each of which outputs an X-ray image, said information processing apparatus comprising:
an information obtaining unit configured to obtain information indicating an output size for each of a first output apparatus and a second output apparatus;
a first setting unit configured to set a first region that is at least a portion of an X-ray image based on the output size of the first output apparatus; and
a second setting unit configured to set a second region that is at least a portion of the first region based on the output size of the second output apparatus.

16. The apparatus according to claim 15, further comprising a transferring unit configured to transfer a first image, which is obtained by extracting a region set by said first setting unit from an X-ray image, to the first output apparatus, and transfer a second image, which is obtained by extracting a region set by the second setting unit from the X-ray image, to the second output apparatus.

17. The apparatus according to claim 16, wherein said first setting unit and said second setting unit set the first region and the second region respectively before imaging of the X-ray image from which the region to be transferred is extracted.

18. The apparatus according to claim 15, further comprising a determining unit configured to determine whether an output size of the second output apparatus is smaller than an output size of the first output apparatus.

19. The apparatus according to claim 15, wherein said second setting unit uses a partial region of the first region as the second region, in a case where the output size of the second output apparatus is smaller than the output size of the second output apparatus.

20. The apparatus according to claim 15, wherein said second setting unit uses the first region as the second region, in a case where the output size of the second output apparatus is not smaller than the output size of the first output apparatus.

21. The apparatus according to claim 15, wherein said first setting unit and said second setting unit preset the first region and the second region respectively for each imaging portion before imaging.

22. The apparatus according to claim 15, wherein a position of the second region, which is set by said second setting unit before imaging of the X-ray image, is changed after imaging of the X-ray image.

23. The apparatus according to claim 15, wherein a size of an irradiated region of an X-ray image is used as the output size of the first output apparatus.

24. The apparatus according to claim 15, wherein said information obtaining unit obtains information indicating maximum size of an X-ray image to be transferred to the first and second output apparatuses respectively as the output sizes of the first and second output apparatuses.

25. An information processing system in which an X-ray image is transferred to a plurality of output apparatuses each of which outputs an X-ray image, said system comprising:
a region obtaining unit configured to obtain an irradiated region on an X-ray image obtained by X-ray imaging;
an information obtaining unit configured to obtain information indicating allowable output size for each of a first output apparatus and a second output apparatus whose allowable output sizes are different from each other; and
a transferring unit configured to transfer a first image to the first output apparatus, which is obtained by extracting at least a portion of the X-ray image based on the irradiated region and allowable output size of the first output apparatus, and transfer a second image to the second output apparatus, which is obtained by extracting at least a portion of the first image based on an allowable output size of the second apparatus.

26. An information processing system in which an X-ray image is transferred to a plurality of output apparatuses each of which outputs an X-ray image, said system comprising:
an information obtaining unit configured to obtain information indicating an output size for each of a first output apparatus and a second output apparatus;
a first setting unit configured to set a first region that is at least a portion of an X-ray image based on the output size of the first output apparatus; and
a second setting unit configured to set a second region that is at least a portion of the first region based on the output size of the second output apparatus.

27. An information processing method of transferring an X-ray image to a plurality of output apparatuses each of which outputs an X-ray image, said method comprising:
a region obtaining step of obtaining an irradiated region on an X-ray image obtained by X-ray imaging;
an information obtaining step of obtaining information indicating allowable output size for each of a first output apparatus and a second output apparatus whose allowable output sizes are different from each other; and
a transferring step of transferring a first image to the first output apparatus, which is obtained by extracting at least a portion of the X-ray image based on the irradiated region and allowable output size of the first output apparatus, and transferring a second image to the second output apparatus, which is obtained by extracting at least a portion of the first image based on an allowable output size of the second apparatus.

28. A non-transitory computer readable storage medium storing a program for causing a computer to execute an information processing method according to claim 27.

29. An information processing method of transferring an X-ray image to a plurality of output apparatuses each of which outputs an X-ray image, said method comprising:
- an information obtaining step of obtaining information indicating an output size for each of a first output apparatus and a second output apparatus;
- a first setting step of setting a first region that is at least a portion of an X-ray image based on the output size of the first output apparatus; and
- a second setting step of setting a second region that is at least a portion of the first region based on the output size of the second output apparatus.

30. A non-transitory computer readable storage medium storing a program for causing a computer to execute an information processing method according to claim 29.

* * * * *